United States Patent
Moriya et al.

(10) Patent No.: US 9,958,386 B2
(45) Date of Patent: May 1, 2018

(54) CHEMICAL SENSOR, CHEMICAL SENSOR MODULE, CHEMICAL SUBSTANCE DETECTION APPARATUS, AND CHEMICAL SUBSTANCE DETECTION METHOD

(71) Applicant: Sony Corporation, Tokyo (JP)

(72) Inventors: Yusuke Moriya, Kanagawa (JP); Nobuyuki Matsuzawa, Tokyo (JP); Kensaku Maeda, Kanagawa (JP)

(73) Assignee: Sony Corporation, Tokyo (JP)

( * ) Notice: Subject to any disclaimer, the term of this patent is extended or adjusted under 35 U.S.C. 154(b) by 873 days.

(21) Appl. No.: 14/358,639

(22) PCT Filed: Nov. 16, 2012

(86) PCT No.: PCT/JP2012/007370
§ 371 (c)(1),
(2) Date: May 15, 2014

(87) PCT Pub. No.: WO2013/080473
PCT Pub. Date: Jun. 6, 2013

(65) Prior Publication Data
US 2014/0329336 A1    Nov. 6, 2014

(30) Foreign Application Priority Data

Nov. 30, 2011    (JP) .................. 2011-262714

(51) Int. Cl.
*G01N 33/551*    (2006.01)
*G01N 21/552*    (2014.01)
*G01N 21/64*    (2006.01)
*G01J 3/44*    (2006.01)

(52) U.S. Cl.
CPC ....... *G01N 21/553* (2013.01); *G01N 21/6454* (2013.01); *G01J 3/4406* (2013.01); *G01N 2021/6471* (2013.01)

(58) Field of Classification Search
None
See application file for complete search history.

(56) References Cited

U.S. PATENT DOCUMENTS

| 6,592,945 B2 * | 7/2003 | Suzuki | B82Y 30/00 427/180 |
| 7,880,175 B2 * | 2/2011 | Shin | H04M 1/22 200/314 |

FOREIGN PATENT DOCUMENTS

| JP | 2002-202303 | 7/2002 |
| JP | 2002-350348 | 12/2002 |
| JP | 2002-350349 | 12/2002 |
| JP | 2003-518924 | 6/2003 |
| JP | 2003-313506 | 11/2003 |
| JP | 2004-205340 | 7/2004 |

* cited by examiner

Primary Examiner — Chris L Chin
(74) Attorney, Agent, or Firm — Chip Law Group (57) ABSTRACT

[Object] To provide a chemical sensor provided with a spectral filter excellent in spectral characteristic, a chemical sensor module, a chemical substance detection apparatus, and a chemical substance detection method.
[Solving Means] A chemical sensor according to the present technology is provided with a substrate and a plasmon absorption layer. On the substrate, the photodetection unit is formed. The plasmon absorption layer is laminated on the substrate and has a metal nanostructure that generates plasmon absorbency.

16 Claims, 8 Drawing Sheets

| Metal nanoparticle containing filter | Organic dye-based filter | Multilayer film filter (TiO$_2$/SiO$_2$) |
|---|---|---|
| 0.25 μm | 1.2 μm | 0.6 μm |

CHEMICAL SENSOR, CHEMICAL SENSOR MODULE, CHEMICAL SUBSTANCE DETECTION APPARATUS, AND CHEMICAL SUBSTANCE DETECTION METHOD

TECHNICAL FIELD

The present technology relates to a chemical sensor, a chemical sensor module, a chemical substance detection apparatus, and a chemical substance detection method for detecting a chemical substance by using light emission on a detection target object.

BACKGROUND ART

A chemical sensor for detecting a chemical substance by using light emission caused by a chemical binding is being studied. Specifically, a probe material that is specifically bound to a target material to be detected is adhered onto a sensor, and a sample containing the target material is supplied to the sensor. As a result, the target material is bound to the probe material. For example, a fluorescent label is introduced to a bound body of the target material and the probe material, and fluorescence is generated on the bound body by irradiation with excitation light. As a result, the fluorescence is detected by a photoelectric conversion element, and thus it is possible to confirm the existence of the target material in the sample.

In such a chemical sensor, if the excitation light for exciting the fluorescent label is detected by the photoelectric conversion element, the excitation light cannot be distinguished from the fluorescence which should be detected, so it is necessary to separate the excitation light from the fluorescence and remove the excitation light.

For example, Patent Document 1 discloses an organic molecule detection semiconductor element provided with an optical filter and DNA immobilization film which blocks out excitation light and causes only fluorescence to pass therethrough. The optical filter and DNA immobilization film is a multilayer film optical filter formed by laminating a silicon dioxide film, an aluminum oxide layer, a magnesium oxide film, and the like and removes ultraviolet light (excitation light) by using interference of light.

Patent Document 1: Japanese Patent Application Laid-open No. 2002-202303 (paragraph [0039], FIG. 1)

SUMMARY OF INVENTION

Problem to be Solved by the Invention

However, the multilayer film optical filter as disclosed in Patent Document 1 requires a certain number of layers in order to sufficiently block out the excitation light, so there is a fear that crosstalk (mixture of light with an adjacent photoelectric conversion element) may be generated due to the large thickness. Further, because the interference of light is used, it is thought that the excitation light that enters the multilayer film optical filter in a slanting direction cannot be effectively blocked out. Furthermore, a great number of processes for forming the multilayer film are required, and thickness control has to be performed, so it is necessary to study productivity.

In view of the circumstances as described above, an object of the present technology is to provide a chemical sensor provided with a spectral filter excellent in spectral characteristic, a chemical sensor module, a chemical substance detection apparatus, and a chemical substance detection method.

Means for Solving the Problem

To achieve the above-mentioned object, a chemical sensor according to an embodiment of the present technology includes a substrate and a plasmon absorption layer.

In the substrate, a photodetection unit is formed.

The plasmon absorption layer is laminated on the substrate, and the plasmon absorption layer has a metal nanostructure that generates plasmon absorbency.

With this structure, it is possible to disperse incident light by the plasmon absorption layer laminated in the upper layer of the substrate and cause only light as a detection target to reach the photodetection unit. By using plasmon absorbency of the metal nanostructure, it is possible to reduce the thickness of the plasmon absorption layer that functions as a spectral filter and prevent fluorescence emission (autofluorescence) on the plasmon absorption layer. Further, the plasmon absorption layer can be more easily produced than a multilayer film filter, which is typical as a spectral filter of a chemical sensor, so it is possible to increase the productivity of the chemical sensor.

The chemical sensor may further include a surface layer laminated on the plasmon absorption layer, the surface layer having a holding surface on which a detection target object is held.

With this structure, by the dispersion by the plasmon absorption layer, it is possible to cause the photodetection unit to detect light emitted from the detection target object held on the holding surface of the surface layer.

The plasmon absorption layer may block out illumination light with which the detection target object is irradiated and may cause detection target light generated on the detection target object to pass therethrough.

With this structure, by the plasmon absorption layer, it is possible to perform dispersion for the illumination light and the detection target light. If the illumination light reaches the photodetection unit, the illumination light is superimposed on the detection target light and is detected by the photodetection unit, resulting in a reduction of the detection accuracy. By blocking out the illumination light by the plasmon absorption layer, it is possible to prevent the illumination light from being detected by the photodetection unit.

The illumination light may be excitation light, and the detection target light may be fluorescence.

With this structure, it is possible to detect the fluorescence with high accuracy. Generally, the fluorescence is weak, so it is necessary to perform exposure for a long time by the photodetection unit. Therefore, in order to improve the detection accuracy, it is necessary to detect only the fluorescence emitted from the detection target object by the photodetection unit. The plasmon absorption layer does not generate autofluorescence and is therefore suitable for the detection of the fluorescence.

The plasmon absorption layer may contain a metal nanoparticle.

By dispersing the metal nanoparticles in synthetic resin or by laminating only the metal nanoparticles, it is possible to form a metal nanostructure having the plasmon absorbency. As the metal nanostructure, there is a metal nanohole in addition thereto, but photolithography or the like has to be performed to produce the metal nanohole. In contrast, by using the metal nanoparticle, it is possible to easily form the metal nanostructure The metal nanoparticle is a particle having a surface formed of one of pure metal containing at least one of gold, silver, and copper and an alloy thereof.

By using such a particle, it is possible to cause the plasmon absorbency. The particle having the surface formed of one of pure metal containing at least one of gold, silver, and copper and the alloy thereof includes a particle made of pure metal of gold, silver, or copper, a particle formed of an alloy containing those, and a core-shell type particle in which a core made of some materials is covered with a shell formed of the pure metal of gold, silver, or copper or the alloy containing those.

The metal nanoparticle may have a particle diameter of 1 nm or more and 150 nm or less.

In the case where the particle diameter of the metal nanoparticle is less than 1 nm, the fluorescence may be generated on the plasmon absorption layer. In the case where the particle diameter thereof exceeds 150 nm, an optical spectrum may be unsuitable for the spectral filter. Therefore, by setting the particle diameter of the metal nanoparticle to fall within the range of 1 nm or more and 150 nm or less, it is possible to make the spectral characteristic of the plasmon absorption layer desirable.

The chemical sensor may further include a color filter layer laminated between the substrate and the plasmon absorption layer, the color filter layer being made of an organic dye-based material.

Upon receiving irradiation of excitation light, the color filter layer made of the organic dye-based material generates fluorescence by itself (autofluorescene), which causes a reduction in detection accuracy of the detection target light. However, with the structure according to the present technology, the color filter layer is disposed below the plasmon absorption layer, with the result that the excitation light is blocked out by the plasmon absorption layer to be prevented from reaching the color filter layer, so the autofluorescence is not generated. At the same time, the color filter has good controllability of blocking/transmission wavelengths, so it is possible to interpolate the spectral characteristic of the plasmon absorption layer by the color filter layer.

The chemical sensor may further include a multilayer film filter layer formed by laminating a plurality of kinds of materials.

With this structure, the multilayer film filter layer and the plasmon absorption layer can complement the spectral characteristics of each other. The multilayer film filter layer does not generate autofluorescence and therefore can be disposed in the upper layer of the plasmon absorption layer.

In the chemical sensor, the holding surface holds a probe material that is specifically bound to a target material to be detected.

With this structure, by supplying a sample containing the target material to the holding surface, it is possible to cause the target material corresponding to the probe material to be bound to the probe material. As a result, detection target light is detected with a bound body of the target material and the probe material as the detection target object, thereby making it possible to check the fact the target material is contained in the sample.

The probe material may be one of DNA, RNA, a protein, and an antigenic substance.

With this structure, it is possible to set those substance as a measurement target.

To achieve the above object, a chemical sensor module according to an embodiment of the present technology includes a chemical sensor and an illumination light source.

The chemical sensor includes a substrate on which a photodetection unit is formed, a plasmon absorption layer laminated on the substrate, and a surface layer laminated on the plasmon absorption layer, the plasmon absorption layer having a metal nanostructure that generates plasmon absorbency, the surface layer having a holding surface on which a detection target object is held.

The illumination light source irradiates the holding surface with illumination light.

To achieve the above object, a chemical substance detection apparatus according to an embodiment of the present technology includes a chemical sensor and a signal processing circuit.

The chemical sensor includes a substrate on which a photodetection unit is formed, a plasmon absorption layer laminated on the substrate, and a surface layer laminated on the plasmon absorption layer, the plasmon absorption layer having a metal nanostructure that generates plasmon absorbency, the surface layer having a holding surface on which a detection target object is held.

The signal processing circuit is connected to the chemical sensor and processes an output signal of the photodetection unit.

To achieve the above object, a chemical substance detection method according to an embodiment of the present technology includes preparing a chemical sensor including a substrate on which a photodetection unit is formed, a plasmon absorption layer laminated on the substrate, and a surface layer laminated on the plasmon absorption layer, the plasmon absorption layer having a metal nanostructure that generates plasmon absorbency, the surface layer having a holding surface on which a detection target object is held.

A probe material is caused to be held on the holding surface.

A sample is brought into contact with the holding surface, and a target material contained in the sample is caused to bind to the probe material to form a detection target object.

The holding surface is irradiated with illumination light.

Upon receiving the illumination light, detection target light generated as a result of binding of the probe material and the target material on the detection target object is detected by the photodetection unit.

The illumination light may be excitation light, and the detection target light may be fluorescence.

In the step of detecting the fluorescence, changes in wavelength and luminance of the fluorescence caused by an interaction of the target material and the probe material fluorescently labeled in advance may be detected by the photodetection unit.

In the step of detecting the fluorescence, the fluorescence generated by the target material that is fluorescently labeled in advance and is bound to the probe material may be detected by the photodetection unit.

In the step of detecting the fluorescence, fluorescent labelling is performed for a bound body of the probe material and the target material, and the fluorescence may be detected by the photodetection unit.

Effect of the Invention

As described above, according to the present technology, it is possible to provide the chemical sensor provided with the spectral filter excellent in spectral characteristic, the chemical sensor module, the chemical substance detection apparatus, and the chemical substance detection method.

BEST MODE(S) FOR CARRYING OUT THE INVENTION

First Embodiment

A chemical substance detection apparatus according to a first embodiment of the present technology will be described.

(Entire Structure of Chemical Substance Detection Apparatus)

Figure 1:
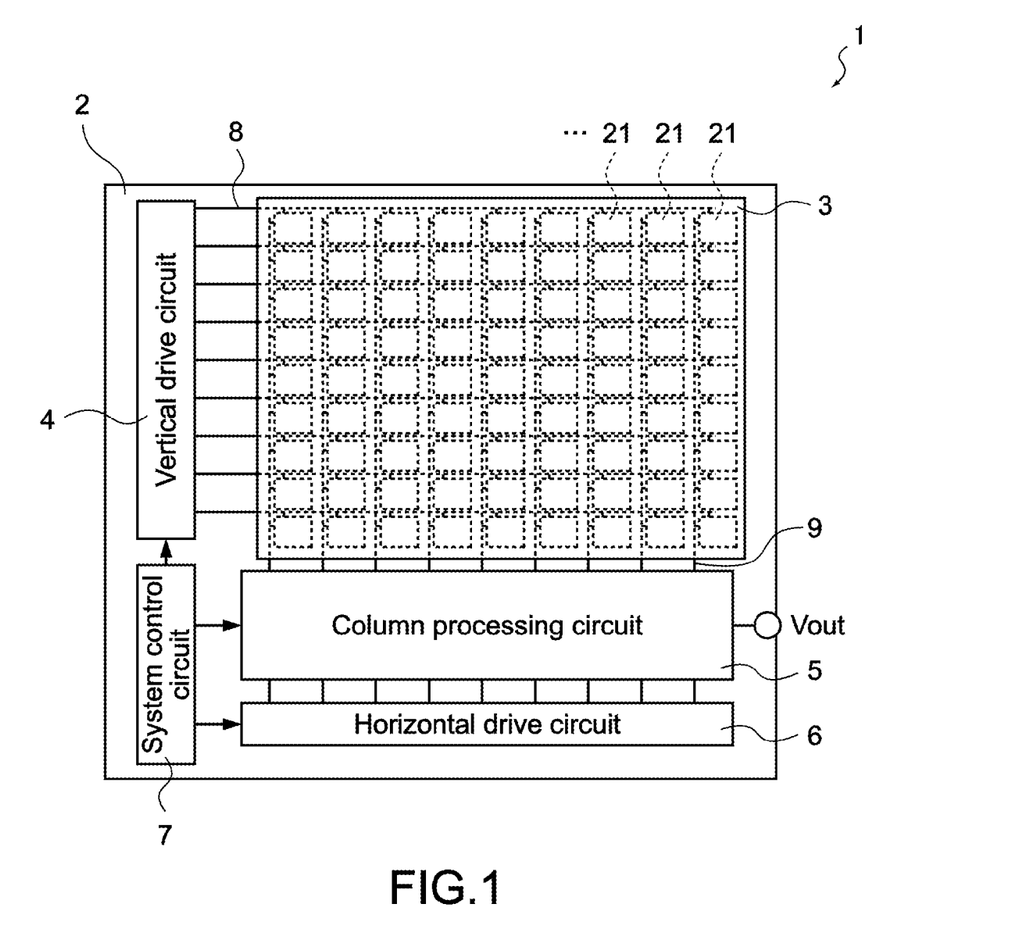
FIG. 1 A schematic diagram showing the structure of a chemical substance detection apparatus according to a first embodiment.

FIG. 1 is a schematic diagram showing the structure of a chemical substance detection apparatus 1 according to this embodiment. As shown in the figure, the chemical substance detection apparatus 1 is constituted of a chemical sensor 3 formed on a substrate 2 and a peripheral circuit for driving the chemical sensor 3. The chemical sensor 3 includes a plurality of photodetection units 21 arranged on the substrate 2.

The number of photodetection units 21 and the arrangement thereof are not limited and can be arranged in a matrix form or a linear form. Here, the photodetection units 21 are arranged in a matrix pattern on a plane of the substrate 2. A row direction is set as a vertical direction, and a column direction is set as a horizontal direction.

The peripheral circuit is constituted of a vertical drive circuit 4, a column signal processing circuit 5, a horizontal drive circuit 6, and a system control circuit 7. Further, the photodetection units 21 are connected to pixel drive lines 8 for each row and connected to vertical signal lines 9 for each column. The pixel drive lines 8 are connected to the vertical drive circuit 4, and the vertical signal lines 9 are connected to the column signal processing circuit 5.

The column signal processing circuit 5 is connected to the horizontal drive circuit 6, and the system control circuit 7 is connected to the vertical drive circuit 4, the column signal processing circuit 5, and the horizontal drive circuit 6. It should be noted that the peripheral circuit can be disposed on a position of being laminated on a pixel area or an opposite side to the substrate 2, for example.

The vertical drive circuit 4 is formed of a shift register, for example. The vertical drive circuit 4 selects the pixel drive line 8, supplies a pulse for driving the photodetection units 21 to the pixel drive line 8 selected, and drives the photodetection units 21 on a row basis. In other words, the vertical drive circuit 4 performs selective scanning for the photodetection units 21 in the vertical direction sequentially on the row basis. Then, through the vertical signal line 9 vertically wired with respect to the pixel drive line 8, the vertical drive circuit 4 supplies, to the column signal processing circuit 5, a pixel signal based on a signal charge generated in accordance with a received light quantity in the photodetection units 21.

The column signal processing circuit 5 performs signal processing such as a noise removal for each pixel column with respect to a signal output from the photodetection units 21 of one row. In other words, the column signal processing circuit 5 performs signal processing such as a correlated double sampling (CDS), a signal amplification, and an analog/digital (AD) conversion for removing a fixed pattern noise specific to a pixel.

The horizontal drive circuit 6 is formed of the shift register, for example, and sequentially outputs horizontal scanning pulses, thereby selecting the column signal processing circuits 5 in order and causing each column signal processing circuit 5 to output a pixel signal.

The system control circuit 7 receives an input clock and data that specifies an operation mode or the like and outputs data relating to inside information or the like of the chemical sensor 3. That is, on the basis of a vertical synchronizing signal, a horizontal synchronizing signal, and a master clock, the system control circuit 7 generates a clock signal and a control signal which are references of the operations of the vertical drive circuit 4, the column signal processing circuit 5, the horizontal drive circuit 6, and the like. Then the system control circuit 7 inputs those signals to the vertical drive circuit 4, the column signal processing circuit 5, the horizontal drive circuit 6, and the like.

As described above, the vertical drive circuit 4, the column signal processing circuit 5, the horizontal drive circuit 6, the system control circuit 7, and a pixel circuit provided to the photodetection units 21 to be described later constitute a drive circuit that drives the photodetection units 21.

(Structure of Chemical Sensor)

Figure 2:
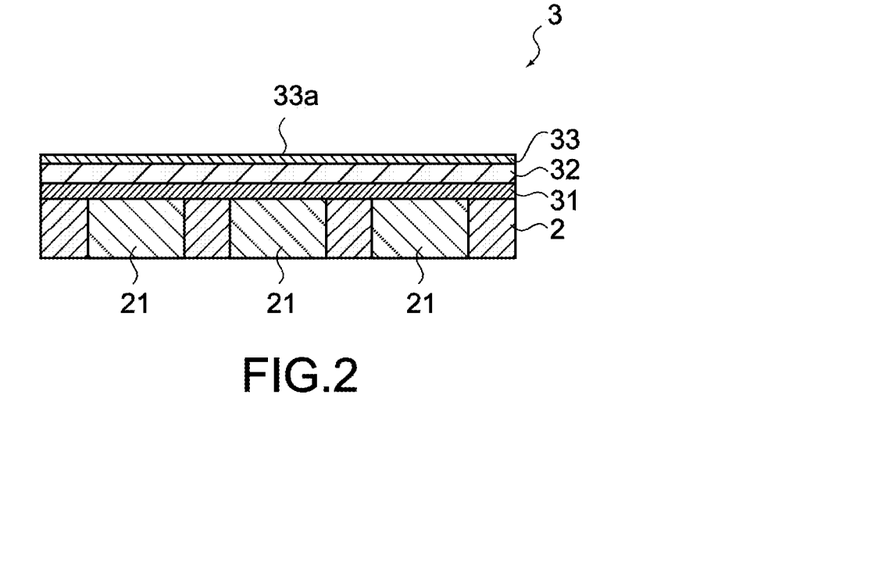
FIG. 2 A schematic diagram showing the structure of a chemical sensor according to the first embodiment.
Figure 3:
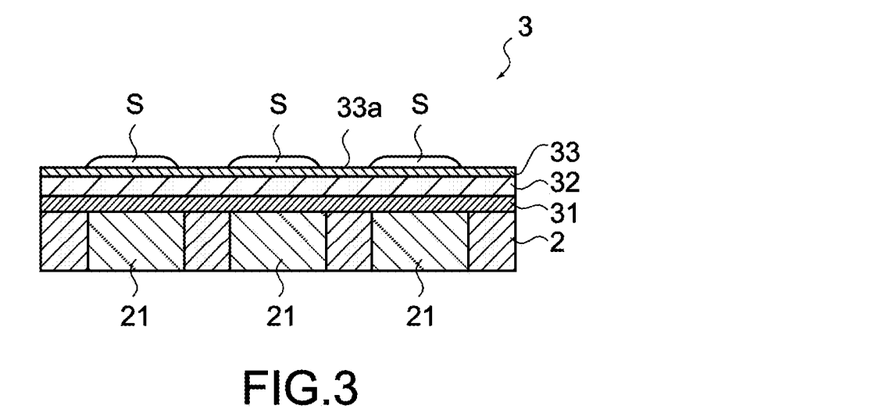
FIG. 3 A schematic diagram showing the structure of the chemical sensor according to the first embodiment.

FIG. 2 is a schematic diagram showing the structure of the chemical sensor 3. As shown in the figure, the chemical sensor 3 is formed by laminating a protection insulating layer 31, a plasmon absorption layer 32, and a surface protection layer 33 in this order on the substrate 2 on which the photodetection units 21 are formed. The chemical sensor 3 is used with a detection target object placed on the surface protection layer 33. FIG. 3 is a schematic diagram showing the chemical sensor 3 on which detection target objects S are placed.

The substrate 2 supports the layers mentioned above and can be made of monocrystalline silicon, for example. The substrate 2 has a principal surface on which the photodetection units 21 are disposed, and on the principal surface, the layers mentioned above are laminated. On the substrate 2, in addition to the photodetection units 21, a structure such as an element isolation and a floating diffusion can be formed.

The photodetection unit 21 can be a photoelectric conversion element (photodiode) that converts light into current. The photodetection unit 21 can be an impurity region formed by introducing impurities onto the substrate 2 as a semiconductor substrate. The photodetection unit 21 can be connected to a pixel circuit formed of a gate insulating film or a gate electrode (not shown), and the pixel circuit can be provided on a surface opposite to the principal surface of the substrate 2.

The protection insulating layer 31 is a layer for protecting and insulating the photodetection units 21 and is made of a material that causes at least a wavelength range of light which is generated on the detection target objects S (hereinafter, referred to as detection target light) to pass therethrough. The protection insulating layer 31 may not be provided depending on the structure of the photodetection unit 21.

The plasmon absorption layer 32 has a metal nanostructure to be described later and is a layer for performing dispersion for light (hereinafter, referred to as illumination light) with which the detection target objects S are irradiated to generate the detection target light and the detection target light. The thickness of the plasmon absorption layer 32 can be sufficiently small as compared to the case of a multilayer film filter or the like on the basis of a spectral principle thereof.

The surface protection layer 33 is a layer for covering and protecting the plasmon absorption layer 32 and holding the detection target objects S. Hereinafter, a surface of the surface protection layer 33 on which the detection target objects S are held is referred to as a holding surface 33a. The surface protection layer 33 is made of a material that causes at least a wavelength range of the detection target light to pass therethrough, such as a silicon dioxide film and a silicon nitride film. Further, for the holding surface 33a, a surface treatment for causing the detection target objects S to adhere to the surface protection layer 33, such as a hydrophilic treatment, may be performed. By such a surface treatment, it is possible to separate an area to which the detection target objects S are adhered (adhesion area) and an area to which the detection target objects S are not adhered (non-adhesion area).

(Chemical Substance Detection Method by Using Chemical Sensor)

A chemical substance detection method by using the chemical sensor 3 described above will be described. It should be noted that the chemical substance detection method to be described below is an example, and the chemical substance detection method by using the chemical sensor 3 is not limited to the method described below.

In the chemical substance detection method using the chemical sensor 3, a probe material capable of being specifically bound to a chemical substance intended to be detected (hereinafter, referred to as target material) can be used.

Specifically, first, the probe material is adhered to the holding surface 33a. For example, in the case where the surface treatment is performed for the holding surface 33a, a solution containing the probe material is dropped on the adhesion area, thereby making it possible to cause the probe material to adhere to the adhesion area. Further, in the case where the holding surface 33a is separated into the adhesion area and the non-adhesion area, probe materials of different kinds may be adhered for each adhesion area.

In this state, a sample solution is supplied onto the holding surface 33a. In the case where the sample solution contains the target material, the target material is bound to the probe material corresponding thereto. The holding surface 33a is washed, thereby removing an extra target material. After that, by introducing a fluorescent label which can be introduced only to a bound body of the probe material and the target material, only the bound body of the probe material and the target material is fluorescently labeled, and the probe material that is not bound to the target material is not fluorescently labeled. It should be noted that in this example, the bound body of the probe material and the target material corresponds to the detection target object S.

In this state, the chemical sensor 3 is irradiated with excitation light from the surface protection layer 33 side. The fluorescent label contained in the detection target object S is excited by the excitation light, and fluorescence is generated. The florescence is transmitted through the surface protection layer 33, the plasmon absorption layer 32, and the protection insulating layer 31, reaches the photodetection units 21, and is detected. The excitation light is blocked out by the plasmon absorption layer 32 and is thus prevented from reaching the photodetection units 21.

In the detection of the target material, for example, in the case where DNA (deoxyribonucleic acid) is used as the probe material, a 5'-fluorescein-labeled DNA can be used. If the sample contains DNA having a sequence complementary to the 5'-fluorescein-labeled DNA, a hybridization reaction occurs, resulting in a change of the probe material from single-stranded DNA (ss-DNA) to double-stranded DNA (ds-DNA). The change causes a permittivity of the surrounding of a fluorescent molecule to change, and thus the change in emission wavelength and intensity of the fluorescence is caused. The change is detected by the photodetection units 21.

Further, in the case where the DNA is used as the probe material, DNA which is not fluorescently labeled is used as the probe material, and the 5'-fluorescein-labeled DNA is used for the sample, for example. In this case, if the sample contains DNA having a sequence complementary to the DNA as the probe material, the hybridization reaction occurs, resulting in a change into ds-DNA with the fluorescent label. The emission of the fluorescence from the fluorescent label is detected by the photodetection units 21.

Alternatively, in the case where the DNA is used as the probe material, DNA which is not fluorescently labeled is used for the probe material, and a fluorescence pigment is not also introduced into the sample side. In this case, if the sample contains DNA having a sequence complementary to the DNA as the probe material, the hybridization reaction occurs, resulting in a change into ds-DNA. Then, a treatment of fluorescent labeling by selectively dying only the ds-DNA is performed by using Pico-Green 2-stranded DNA quantification reagent produced by Molecular Probes, for example, thereby introducing the fluorescent label into the ds-DNA part. The emission of the fluorescence from the fluorescent label is detected by the photodetection units 21.

In the above example, the description is given with the probe material as the DNA, but it is possible to use various biomolecules such as RNA (ribo nucleic acid), proteins, and antigenic substances or various chemical substances as the probe material. Further, as an example of the illumination light with which the detection target objects S are irradiated, the excitation light is given, and as the detection target light emitted from the detection target objects S, the fluorescence is given, but the illumination light and the detection target light are not limited thereto. As long as there is such a relationship that the detection target objects S are irradiated with any light, and the detection target objects S emit any light with a different wavelength, the present technology can be applied.

(About Dispersing by Plasmon Absorption Layer)

As described above, the plasmon absorption layer 32 blocks out the illumination light and causes only the detection target light to pass therethrough. That is, the plasmon absorption layer 32 functions as a spectral filter. The plasmon absorption layer 32 has a metal nanostructure, that is, a nano-size structure formed of metal, such as a metal nanoparticle and a metal nanohole.

The plasmon absorption layer 32 has plasmon absorbency. The plasmon refers to a quantum of collective oscillation of free electrons in metal. In the metal nanostructure, a surface plasmon with oscillation different from bulk metal is generated. The interaction between the surface plasmon and light is referred to as a surface plasmon resonance, and an optical electric field of a specific wavelength determined depending on a metal type, a nanostructure shape (particle shape, hole shape, or the like), and a nanostructure size (particle size, hole diameter, or the like) and the plasmon are subjected to coupling, with the result that light absorption is caused.

Specifically, in this embodiment, it is possible to use a metal nanoparticle having a surface formed of pure metal containing at least one of gold, silver, and copper or an alloy thereof. This includes a particle made of pure metal of gold, silver, or copper, a particle formed of an alloy containing at least one of gold, silver, and copper, and a core-shell type particle formed by covering some metal core or non-metal core with a shell made of the pure metal or the alloy.

It is desirable that the particle diameter of the metal nanoparticle is 1 nm or more and 150 nm or less. In the case where the particle diameter of the metal nanoparticle is less than 1 nm, fluorescence may be generated in the metal nanoparticle. In addition, in the case where the particle diameter exceeds 150 nm, an optical spectrum may be unsuitable for the spectral filter. Specifically, it is thought that designing of blocking/transmission wavelength becomes difficult, for example, two or more transmission peaks of the optical spectrum are generated.

Figure 4:
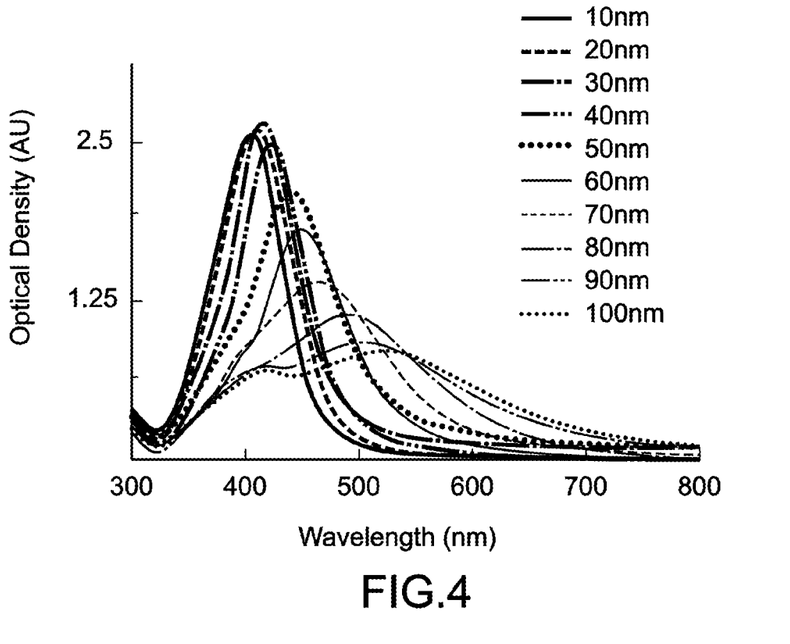
FIG. 4 A graph showing an absorption spectrum based on particle sizes of silver nanoparticles.
Figure 5:
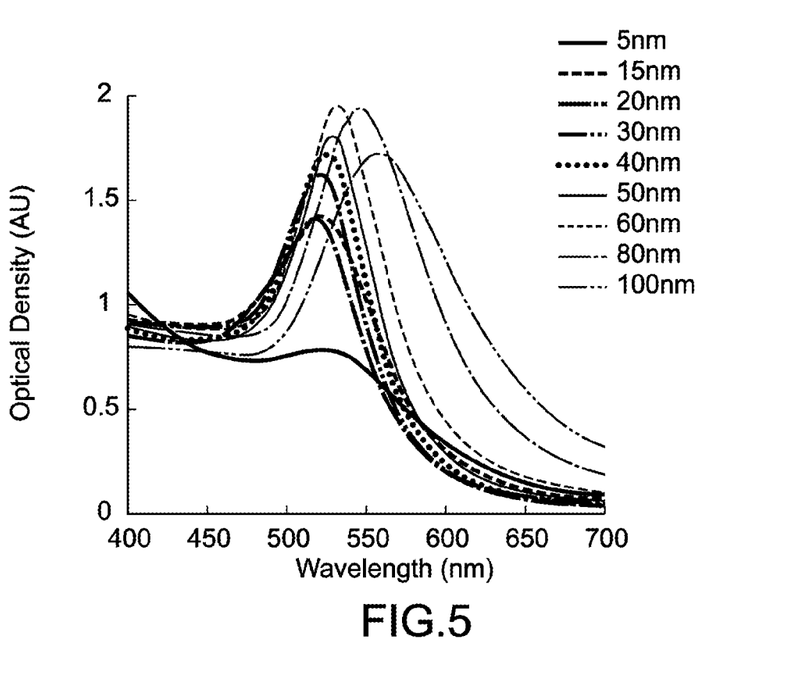
FIG. 5 A graph showing an absorption spectrum based on particle sizes of gold nanoparticles.

FIG. 4 shows an absorption spectrum based on particle sizes of silver nanoparticles, and FIG. 5 shows an absorption spectrum based on gold nanoparticles. It is found that, from FIG. 4, a wavelength range of maximum absorption is generated at approximately 400 nm for the silver nanoparticles, and from FIG. 5, a wavelength range of maximum absorption is generated at approximately 520 nm for the gold nanoparticles. In both the cases of the silver nanoparticles and the gold nanoparticles, the wavelength ranges of absorption are shifted depending on the particle sizes, but a difference in metal type gives a larger influence.

Figure 6:
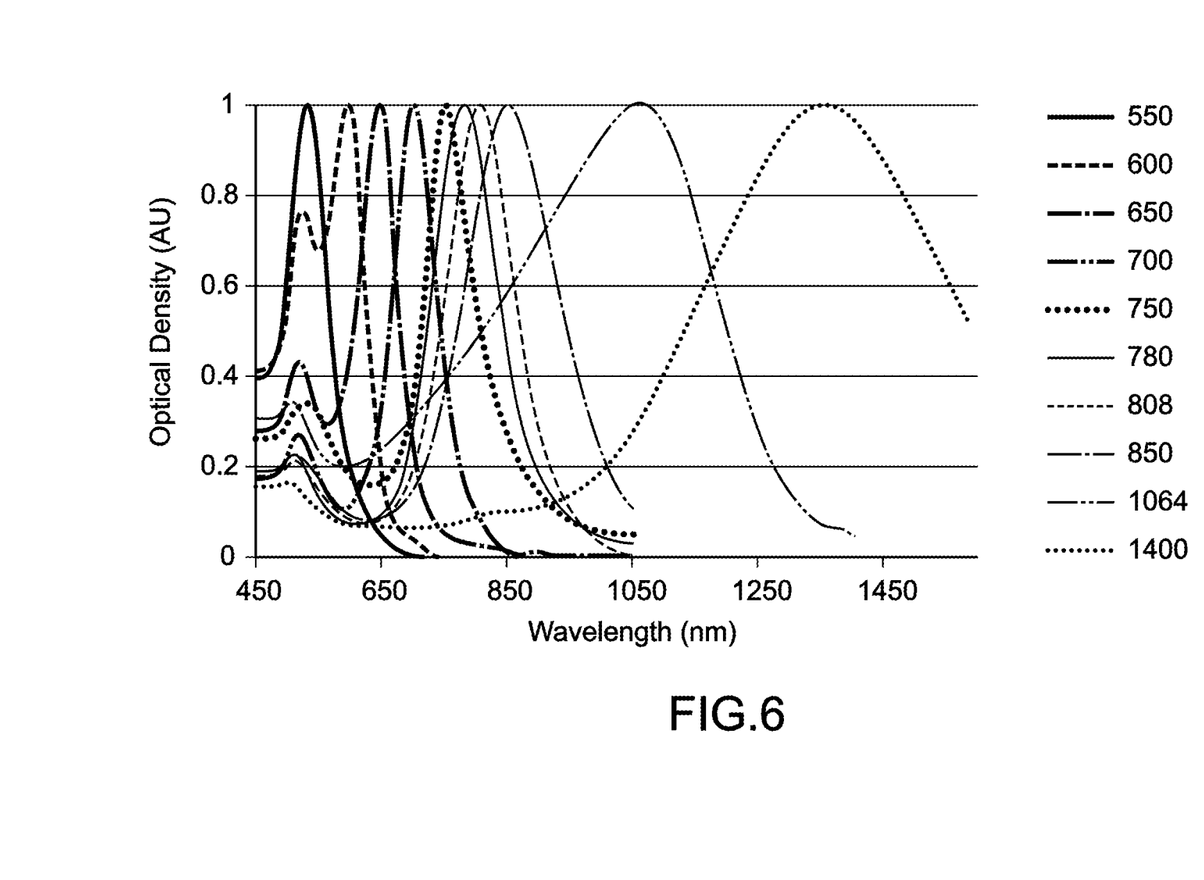
FIG. 6 An absorption spectrum based on particle sizes of gold nanoparticles (rod shape).
Figure 7:
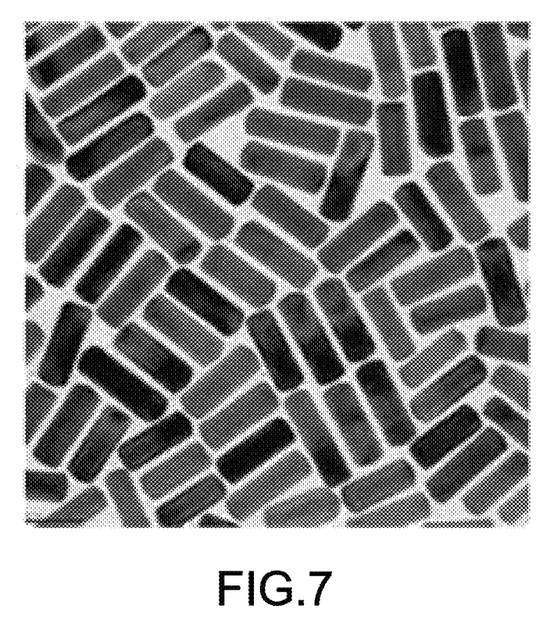
FIG. 7 A TEM image of the gold nanoparticles (rod shape).

FIG. 6 shows an absorption spectrum based on particle sizes (rod lengths) of rod-shaped gold nanoparticles. FIG. 7 shows a TEM (transmission electron microscope) image of the rod-shaped gold nanoparticles (10 nm×40 nm). As shown in FIG. 6, in the case of the rod-shaped gold nanoparticles, the wavelength range of maximum absorption varies from 500 nm to 1400 nm depending on the particle sizes. In this way, by appropriately selecting the metal type of the metal nanoparticles contained in the plasmon absorption layer 32, the particle shape, and the particle size, it is possible to set any wavelength range to the wavelength range of absorption of the plasmon absorption layer 32.

As described above, in this embodiment, by using the plasmon absorbency of the metal nanostructure, the absorption wavelength range of the metal nanostructure is set to the wavelength range of the illumination light, with the result that the plasmon absorption layer 32 can be used as the spectral filter.

The use of the plasmon absorption layer 32 as the spectral layer provides the following advantages relative to a typical multilayer film filter or a typical organic dye-based filter (color filter).

Figure 8:
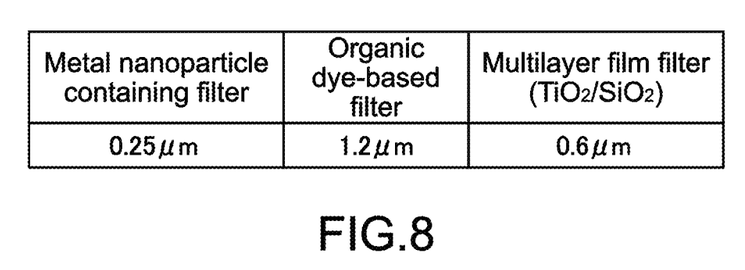
FIG. 8 A table showing necessary thicknesses depending on filter structures.

First, it is possible to reduce the thickness necessary to obtain sufficient spectral characteristic. FIG. 8 shows thicknesses necessary to achieve a transmittance of 0.1% with respect to light with a wavelength of 530 nm. As shown in the figure, a spectral filter (metal nanoparticle containing filter) that uses the metal nanoparticles has the necessary thickness smaller than the organic dye-based filter and the multilayer film filter ($TiO_2/SiO_2$). Therefore, the detection target object S and the photodetection unit 21 are closer to each other, so it is possible to prevent such a phenomenon (crosstalk) that the detection target light generated on the detection target object S is detected by the adjacent photodetection unit 21.

Further, autofluorescence, which is a problem in the case of the organic dye-based filter, is not generated. The autofluorescence is a phenomenon that the spectral filter itself is excited by excitation light to generate fluorescence. If the autofluorescence is generated, the autofluorescence is mixed in the fluorescence generated on the detection target object, resulting in a reduction in measurement accuracy of the photodetection unit.

Figure 9:
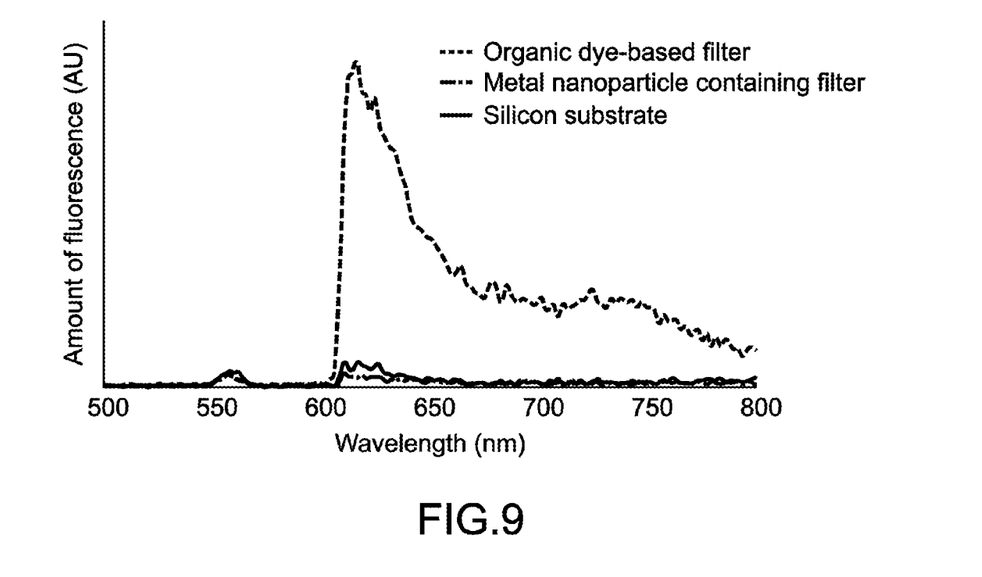
FIG. 9 A graph showing a fluorescence spectrum of various filters.

FIG. 9 is a graph showing a fluorescence measurement result of the metal nanoparticle containing filter, the organic dye-based filter, and the silicon substrate. The silicon substrate is used as reference, and the metal nanoparticle containing filter is obtained by coating the silicon substrate with the metal nanoparticles. The wavelength of the excitation light ranges from 510 nm to 550 nm, and the detection wavelength of the fluorescence is 600 nm or more. As shown in the figure, it is found that the autofluorescence is generated on the organic dye-based filter but is not generated on the metal nanoparticle containing filter. In this way, in the spectral filter that uses the metal nanoparticles according to the present technology, the autofluorescence is not generated, so it is possible to measure the detection target light with high accuracy.

Further, for the multilayer film filter, it is necessary to laminate a plurality of layers in accurate thicknesses. In contrast, for the plasmon absorption layer 32, only one layer is used, and the thickness thereof may be set less accurately than the multilayer film filter. Therefore, by using the plasmon absorption layer 32 for the spectral filter, it is possible to increase the productivity of the chemical sensor 3.

In addition, on the basis of the spectral principle in which a light interference is used, the multilayer film filter has a spectral function with respect to incident light in a direction vertical to the layer but cannot perform effective dispersion with respect to incident light in a slanting direction. In contrast, the plasmon absorption layer 32 according to this embodiment has the advantage over the multilayer film filter in that an incident angle that allows effective dispersion is wider without a limitation on the incident angle unlike the multilayer film filter.

(Chemical Sensor Module)

Figure 10:
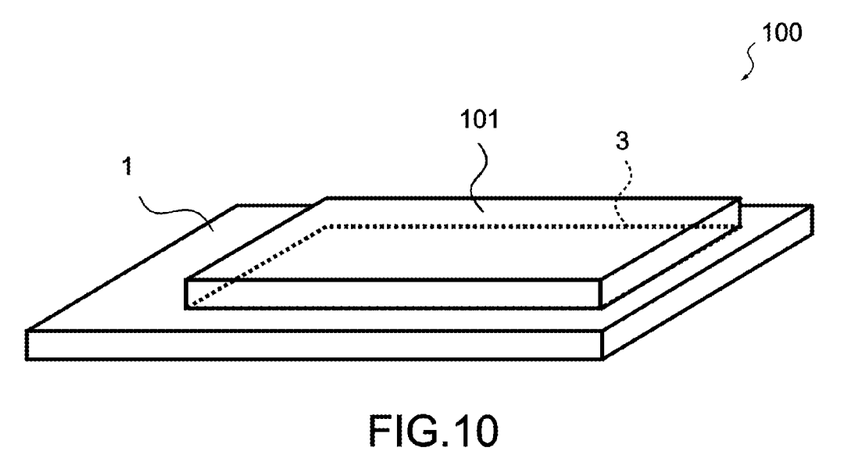
FIG. 10 A schematic diagram showing the structure of a chemical sensor module according to the first embodiment.

The chemical sensor 3 can form a module with an illumination light source that emits illumination light to the chemical sensor 3. FIG. 10 is a schematic diagram showing a chemical sensor module 100. As shown in the figure, the chemical sensor module 100 is constituted by integrally connecting an illumination light source 101 to the chemical sensor 3. The illumination light emitted from the illumination light source 101 enters the detection target objects S held on the holding surface 33a and causes the detection target light to generate. It should be noted that the plasmon absorption layer 32 according to this embodiment can effectively disperse the light incident on the layer in a slanting direction, so such a light source can be used as the illumination light source 101.

(Method of Manufacturing Chemical Sensor)

A method of manufacturing the chemical sensor 3 will be described (see, FIG. 1). First, on the principal surface of the substrate 2, the photodetection units 21 formed of impurity regions, a gate insulating film (not shown), and a gate electrode (not shown) by ion implantation through a mask and a thermal treatment thereafter. Then, on the substrate 2 on which the photodetection units 21 are formed, the protection insulating layer 31 is laminated by a CVD (Chemical Vapor Deposition), a sputtering method, or the like.

Then, on the protection insulating layer 31, the plasmon absorption layer 32 is laminated. In the case of being formed of the metal nanoparticles, the plasmon absorption layer 32 can be formed by performing spin coating, mist coating, an inkjet method, or the like of resin containing the metal nanoparticles or a metal nanoparticle solution. Further, in the case of being formed of the metal nanoholes, the plasmon absorption layer 32 can be formed by patterning a metal film by photolithography or the like.

Then, on the plasmon absorption layer 32, the surface protection layer 33 is laminated. The surface protection layer 33 can be laminated by the CVD method, the sputtering method, or the like. It should be noted that it is also possible to laminate the plasmon absorption layer 32 by the inkjet method on a wafer chip after the protection insulating layer 31 is laminated, PAD opening is performed, and a post-process is performed.

As described above, according to this embodiment, the plasmon absorption layer 32 is used as the spectral filter, with the result that the effective dispersion can be performed, and the chemical sensor 3 provided with the optical filter with high productivity can be provided.

Second Embodiment

A chemical substance detection apparatus according to a second embodiment of the present technology will be described. It should be noted that in this embodiment, structures which are the same as those in the first embodiment are denoted by the same reference symbols, and descriptions thereof will be omitted.

Figure 11:
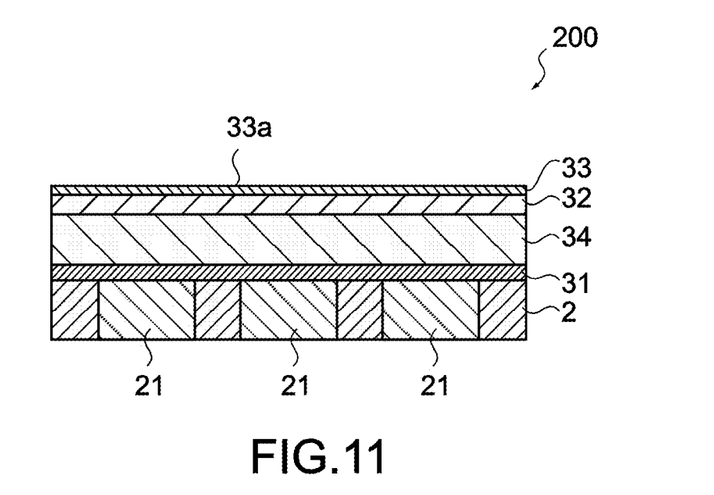
FIG. 11 A schematic diagram showing the structure of a chemical sensor module according to a second embodiment.

The chemical substance detection apparatus according to this embodiment is different from the chemical substance detection apparatus according to the first embodiment in terms of the structure of a chemical sensor. FIG. 11 is a schematic diagram showing the structure of a chemical sensor 200 according to this embodiment.

As shown in FIG. 11, the chemical sensor 200 includes a color filter layer 34, in addition to the substrate 2 on which the photodetection units 21 are formed, the protection insulating layer 31, the plasmon absorption layer 32, and the surface protection layer 33. The color filter layer 34 is laminated between the protection insulating layer 31 and the plasmon absorption layer 32, that is, on a lower layer side of the plasmon absorption layer 32.

The color filter layer 34 is made of organic dye-based resin and disperses incident light by a color thereof. The color filter layer 34 can be made of a material having an appropriate spectral characteristic in accordance with wavelength ranges of the illumination light and the detection target light.

As described above, the color filter made of the organic dye-based resin may generate autofluorescence, which is the fluorescence generated by receiving excitation light irradiation. However, in the chemical sensor 200 according to this embodiment, in the upper layer of the color filter layer 34, the plasmon absorption layer 32 is provided, so the excitation light is blocked out by the plasmon absorption layer 32, with the result that the autofluorescence by the color filter layer 34 is prevented.

On another front, it is easy to control the absorption and transmission wavelength of the color filter. Thus, by disposing the color filter layer 34 in the lower layer of the plasmon absorption layer 32, it is possible to perform dispersion in accordance with the wavelength ranges of the illumination light and the detection target light, while preventing the generation of the autofluorescence. In other words, it is sufficient that the plasmon absorption layer 32 blocks out only a wavelength range in which the autofluorescence is generated by the color filter 34, that is, the color filter 34 is used, thereby making it easy to perform optical design of the plasmon absorption layer 32.

Third Embodiment

A chemical substance detection apparatus according to a third embodiment of the present technology will be described. It should be noted that in this embodiment, structures which are the same as those in the first embodiment are denoted by the same reference symbols, and descriptions thereof will be omitted.

Figure 12:
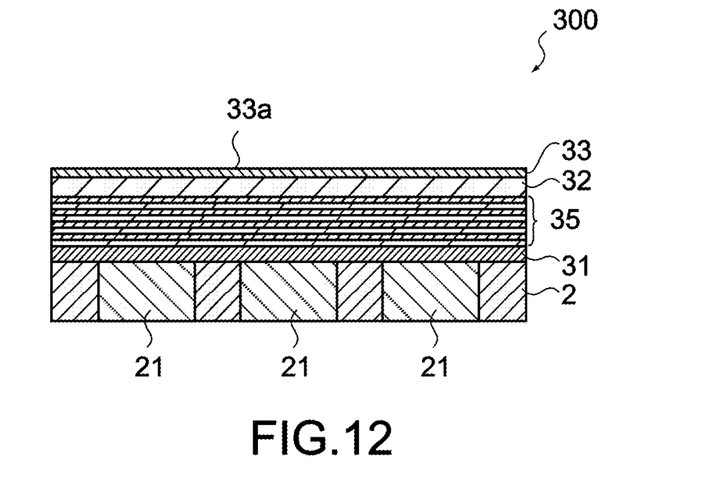
FIG. 12 A schematic diagram showing the structure of a chemical sensor module according to a third embodiment.

The chemical substance detection apparatus according to this embodiment is different from the chemical substance detection apparatus according to the first embodiment in terms of the structure of a chemical sensor. FIG. 12 is a schematic diagram showing the structure of a chemical sensor 300 according to this embodiment.

As shown in FIG. 12, the chemical sensor 300 includes a multilayer film filter layer 35, in addition to the substrate 2 on which the photodetection units 21 are formed, the protection insulating layer 31, the plasmon absorption layer 32, and the surface protection layer 33. The multilayer film filter layer 35 is laminated between the protection insulating layer 31 and the plasmon absorption layer 32. In addition, although not shown, the multilayer film filter layer 35 may be laminated between the plasmon absorption layer 32 and the protection insulating layer 31.

The multilayer film filter layer 35 is formed by alternately laminating a plurality of materials such as $TiO_2$ and $SiO_2$ and disperses incident light by a light interference. The multilayer film filter layer 35 can be made of a material having an appropriate spectral characteristic in accordance with the wavelength ranges of the illumination light and the detection target light.

In the multilayer film filter layer 35, unlike the color filter, the autofluorescence is not generated, so the multilayer film filter layer 35 can be formed in the upper layer of the plasmon absorption layer 32, instead of being formed in the lower layer of the plasmon absorption layer 32. By using the multilayer film filter layer 35, it is possible to mutually interpolate the spectral characteristics of the plasmon absorption layer 32 and the multilayer film filter layer 35 and reduce the number of required layers of the multilayer film filter layer 35.

The present technology is not limited to the above embodiments and can be modified without departing from the gist of the present technology.

The plasmon absorption layer described in the above embodiments, that is, the spectral filter using the plasmon absorbency by the metal nanostructures can be used for another device other than the chemical sensor. For example, the plasmon absorption layer can be used as a spectral filter of a health-care sensor that irradiates a finger of a test subject with infrared rays and detect a displacement in reflection, absorption, or the like thereof.

It should be noted that the present technology can take the following configuration.

(1) A chemical sensor, including:
a substrate on which a photodetection unit is formed; and
a plasmon absorption layer laminated on the substrate, the plasmon absorption layer having a metal nanostructure that generates plasmon absorbency.

(2) The chemical sensor according to Item (1), further including
a surface layer laminated on the plasmon absorption layer, the surface layer having a holding surface on which a detection target object is held.

(3) The chemical sensor according to Item (1) or (2), in which
the plasmon absorption layer blocks out illumination light with which the detection target object is irradiated and causes detection target light generated on the detection target object to pass therethrough.

(4) The chemical sensor according to any one of Items (1) to (3), in which
the illumination light is excitation light, and
the detection target light is fluorescence.

(5) The chemical sensor according to any one of Items (1) to (4), in which
the plasmon absorption layer contains a metal nanoparticle.

(6) The chemical sensor according to any one of Items (1) to (5), in which
the metal nanoparticle is a particle having a surface formed of one of pure metal containing at least one of gold, silver, and copper and an alloy thereof.

(7) The chemical sensor according to any one of Items (1) to (6), in which
the metal nanoparticle has a particle diameter of 1 nm or more and 150 nm or less.

(8) The chemical sensor according to any one of Items (1) to (7), further including
a color filter layer laminated between the substrate and the plasmon absorption layer, the color filter layer being made of an organic dye-based material.

(9) The chemical sensor according to any one of Items (1) to (8), further including
a multilayer film filter layer formed by laminating a plurality of kinds of materials.

(10) The chemical sensor according to any one of Items (1) to (9), in which
the holding surface holds a probe material that is specifically bound to a target material to be detected.

(11) The chemical sensor according to any one of Items (1) to (10), in which
the probe material is one of DNA, RNA, a protein, and an antigenic substance.

(12) A chemical sensor module, including:
a chemical sensor including a substrate on which a photodetection unit is formed, a plasmon absorption layer laminated on the substrate, and a surface layer laminated on the plasmon absorption layer, the plasmon absorption layer having a metal nanostructure that generates plasmon absorbency, the surface layer having a holding surface on which a detection target object is held; and
an illumination light source that irradiates the holding surface with illumination light.

(13) A chemical substance detection apparatus, including:
a chemical sensor including a substrate on which a photodetection unit is formed, a plasmon absorption layer laminated on the substrate, and a surface layer laminated on the plasmon absorption layer, the plasmon absorption layer having a metal nanostructure that generates plasmon absorbency, the surface layer having a holding surface on which a detection target object is held; and
a signal processing circuit that is connected to the chemical sensor and processes an output signal of the photodetection unit.

(14) A chemical substance detection method, including:
preparing a chemical sensor including a substrate on which a photodetection unit is formed, a plasmon absorption layer laminated on the substrate, and a surface layer laminated on the plasmon absorption layer, the plasmon absorption layer having a metal nanostructure that generates plasmon absorbency, the surface layer having a holding surface on which a detection target object is held;
causing a probe material to be held on the holding surface;
bringing a sample into contact with the holding surface and causing a target material contained in the sample to bind to the probe material to form a detection target object;
irradiating the holding surface with illumination light; and
detecting, by the photodetection unit, detection target light generated as a result of binding of the probe material and the target material on the detection target object upon receiving the illumination light.

(15) The chemical substance detection method according to Item (14), in which
the illumination light is excitation light, and
the detection target light is fluorescence.

(16) The chemical substance detection method according to Item (14) or (15), in which
in the step of detecting the fluorescence, changes in wavelength and luminance of the fluorescence caused by an interaction of the target material and the probe material fluorescently labeled in advance are detected by the photodetection unit.

(17) The chemical substance detection method according to any one of Items (14) to (16), in which
in the step of detecting the fluorescence, the fluorescence generated by the target material that is fluorescently labeled in advance and is bound to the probe material is detected by the photodetection unit.

(18) The chemical substance detection method according to any one of Items (14) to (17), in which
in the step of detecting the fluorescence, fluorescent labelling is performed for a bound body of the probe material and the target material, and the fluorescence is detected by the photodetection unit.

DESCRIPTION OF SYMBOLS 1 chemical substance detection apparatus
2 substrate
3 chemical sensor
21 photodetection unit
31 protection insulating layer
32 plasmon absorption layer
33 surface protection layer 33a holding surface
34 color filter layer
35 multilayer film filter layer
100 chemical sensor module
101 illumination light
200 chemical sensor
300 chemical sensor

The invention claimed is:

1. A sensor, comprising:
a substrate;
at least one photodetection unit is diffused as impurity in the substrate; and
a plasmon absorption layer laminated on the substrate, wherein the plasmon absorption layer having a metal nanostructure that generates plasmon absorbency,
wherein the plasmon absorption layer contains a metal nanoparticle and the metal nanoparticle has a particle diameter of 1 nm or more and 150 nm or less.

2. The sensor according to claim 1, further comprising a surface layer laminated on the plasmon absorption layer, wherein the surface layer having a holding surface on which a detection target object is held.

3. The sensor according to claim 2, wherein the plasmon absorption layer blocks out illumination light with which the detection target object is irradiated, and wherein the sensor further includes a fluorescent label that generates detection target light on the detection target object to pass therethrough.

4. The sensor according to claim 3, wherein
the illumination light is excitation light, and
the detection target light is fluorescence.

5. The sensor according to claim 2, wherein
the holding surface holds a probe material that is specifically bound to a target material to be detected.

6. The sensor according to claim 5, wherein
the probe material is one of DNA, RNA, a protein, or an antigenic substance.

7. The sensor according to claim 1, wherein
the metal nanoparticle is a particle having a surface of a metal that contains at least one of gold, silver, or copper and an alloy thereof.

8. The sensor according to claim 1, further comprising
a color filter layer laminated between the substrate and the plasmon absorption layer, wherein a material of the color filter layer is an organic-dye based resin.

9. The sensor according to claim 1, further comprising
a multilayer film filter layer that is based on an alternate lamination of a plurality of material that comprises $TiO_2$ and $SiO_2$.

10. A sensor module, comprising:
a sensor including a substrate;
at least one photodetection unit that is diffused as impurity in the substrate;
a plasmon absorption layer laminated on the substrate, and a surface layer laminated on the plasmon absorption layer, wherein the plasmon absorption layer having a metal nanostructure that generates plasmon absorbency, wherein the plasmon absorption layer contains a metal nanoparticle and the metal nanoparticle has a particle diameter of 1 nm or more and 150 nm or less, and wherein the surface layer having a holding surface on which a detection target object is held; and
an illumination light source that irradiates the holding surface with illumination light.

11. A detection apparatus, comprising:
a sensor including a substrate;
at least one photodetection unit that is diffused as impurity in the substrate;
a plasmon absorption layer laminated on the substrate, and a surface layer laminated on the plasmon absorption layer, wherein the plasmon absorption layer having a metal nanostructure that generates plasmon absorbency, wherein the plasmon absorption layer contains a metal nanoparticle and the metal nanoparticle has a particle diameter of 1 nm or more and 150 nm or less, and wherein the surface layer having a holding surface on which a detection target object is held; and
a signal processing circuit that is connected to the sensor, wherein the signal processing circuit process an output signal of the at least one photodetection unit.

12. A detection method, comprising:
preparing a sensor including a substrate;
diffusing at least one photodetection unit as impurity in the substrate;
laminating, a plasmon absorption layer on the substrate, a surface layer on the plasmon absorption layer, wherein the plasmon absorption layer having a metal nanostructure that generates plasmon absorbency, wherein the plasmon absorption layer contains a metal nanoparticle and the metal nanoparticle has a particle diameter of 1 nm or more and 150 nm or less, and wherein the surface layer having a holding surface on which a detection target object is held;
causing a probe material to be held on the holding surface;
bringing a sample into contact with the holding surface and causing a target material contained in the sample to bind to the probe material to provide the detection target object, wherein a fluorescent label is introduced to at least one of a bound body of the probe material and the target material;
irradiating the holding surface with illumination light; and
detecting, by the at least one photodetection unit, detection target light generated based on the fluorescent label as a result of binding of the probe material and the target material on the detection target object upon receiving the illumination light.

13. The detection method according to claim 12, wherein
the illumination light is excitation light, and
the detection target light is fluorescence.

14. The detection method according to claim 13, further comprising
washing the holding surface before the fluorescent label is introduced to the at least one of a bound body of the probe material and the target material; and
detecting, by the at least one photodetection unit, changes in wavelength and luminance of the fluorescence caused by an interaction of the target material and the probe material fluorescently labeled in advance, to further detect the fluorescence.

15. The detection method according to claim 13, further comprising
detecting, by the at least one photodetection unit, the fluorescence generated based on the target material that is labeled based on the fluorescent label, wherein the target material is bound to the probe material.

16. The detection method according to claim 13, further comprising:
labelling of the fluorescent label for a bound body of the probe material and the target material, and
detecting the fluorescence by the at least one photodetection unit.

* * * * *